United States Patent [19]

Norris

[11] Patent Number: 4,909,263

[45] Date of Patent: Mar. 20, 1990

[54] METHOD AND APPARATUS FOR FITTING A PATIENT WITH A BODY CAVITY ELECTRODE

[75] Inventor: Steven A. Norris, Conyers, Ga.

[73] Assignee: C. R. Bard, Inc., Murray Hill, N.J.

[21] Appl. No.: 264,019

[22] Filed: Oct. 28, 1988

[51] Int. Cl.$^4$ .............................................. A61N 1/00
[52] U.S. Cl. .................................... 128/788; 128/738; 128/778
[58] Field of Search ...................... 128/303.13–303.17, 128/341–343, 738, 778, 784, 788; 604/117

[56] References Cited

U.S. PATENT DOCUMENTS

| | | | |
|---|---|---|---|
| 3,800,800 | 4/1974 | Garbe et al. | 128/788 |
| 3,933,147 | 1/1976 | Du Vall et al. | 128/778 |
| 4,050,449 | 9/1977 | Costellana et al. | 128/778 |
| 4,224,949 | 9/1980 | Scott et al. | 127/738 |
| 4,362,167 | 12/1982 | Nicolai et al. | 128/778 |
| 4,515,167 | 5/1985 | Hochman | 128/738 |
| 4,765,331 | 8/1988 | Petruzzi et al. | 128/303.14 |
| 4,785,828 | 11/1988 | Maurer | 128/788 |

FOREIGN PATENT DOCUMENTS 0221635  5/1985  German Democratic Rep. ..................... 128/738

Primary Examiner—Max Hindenburg
Attorney, Agent, or Firm—Dennison, Meserole, Pollack & Scheiner

[57] ABSTRACT

An elongate relatively rigid and electrically insulated vehicle is disclosed for use in fitting a vaginal or anal electrical stimulator used in treatment of urinary incontinence or sexual disfunction. The vehicle has spaced electrodes along its length which may be selectively actuated by a control unit to apply a pulsing voltage to the pelvic floor muscles. Pressure transducers located adjacent the electrodes measure the pressure applied by the muscles on the canal wall and a scale on the proximal end of the vehicle is used to determine the proper positioning of the electrodes and length of the vehicle for use in fashioning and fitting the patient with a proper electrical stimulator. A method for fitting the patient with such a stimulator using the vehicle is also disclosed.

15 Claims, 1 Drawing Sheet

METHOD AND APPARATUS FOR FITTING A PATIENT WITH A BODY CAVITY ELECTRODE

BACKGROUND OF THE INVENTION

1. Field of the Invention

This invention relates to means for taking body cavity recordings of pressure and of electromyography (EMG) during electrical stimulation for the principal purpose of properly fitting a patient with an electrical stimulator treatment device and also for diagnosing and monitoring of treatment. While this disclosure relates to use in body cavities broadly, it is principally used intravaginally or intrarectally.

Urinary incontinence is a common problem throughout the world and is particularly prevalent in the female population and in the aged. Resulting from incontinence is embarrassment, significant patient discomfort and distress, loss of sleep and the necessity for large monetary disbursements by the patient for absorbent pads, diapers, rubber sheeting and for cleaning of soiled clothing. Currently, treatments of choice consist of surgery, physical exercises and drug therapy.

Functional electrical stimulation has shown promise as an alternative treatment and the same is of course noninvasive, safe in use and relatively inexpensive. The use of intravaginal, intrarectal and transcutaneous electrical stimulation has been known for over fifteen years both in the United States and in Europe and the mechanisms of action are fully documented and well known.

Electrical stimulation of the various branches of the pudendal nerve which lead to the muscles of the pelvic floor have been found to cause contraction of these muscles acutely and strengthening of the muscles during chronic stimulation. With adequate and timely electrical stimulation in this manner, the patient may be completely cured of incontinence and may no longer require further assistance or treatment. It may however require many months of stimulation to reach this result.

There are also reflex pathways involving the pudendal, parasympathetic, sympathetic and somatic nerves which converge on the micturition center of the body located in the spinal cord to produce bladder inhibition and pelvic floor sphincter contraction, both urinary and anal. These known stimulating devices may be employed for both stress-type incontinence with pelvic floor weakness and urge-type incontinence with bladder hyper-irritability, or even mixtures of these two types.

It has also been found that such stimulators are effective in the treatment of certain sexual dysfunctions which are common in these patient populations with similar nerve pathway problems. These include erectile and ejaculatory problems in the male and functional problems including infertility in the female.

2. Prior Art

Examples of electrical stimulation devices for use in the treatment of incontinence and sexual dysfunction are found in the following U.S. Pat. Nos.: 3,518,997-Sessions, 3,623,486-Berkovitz, 3,631,860-Lopin, 4,102,344-Conway et al., 4,569,351-Tang, 4,577,640-Hofmeister, and 4,515,167-Hochman.

Typical prior art devices include an elongated cylindrical intravaginal insert or vehicle formed from electrical insulating material which is substantially rigid and of such a size as to fit completely within the vagina. Two or more electrodes encircle the insert and are spaced apart along the length thereof and are connected via a wire running internally of the insert to a source of electrical potential. The positioning of the electrodes is critical and they must be in the proper location to contact the appropriate area on vaginal wall so that the stimulation activates the pelvic floor muscle. This position is also critical so that it activates reflex pathways. The electrical signal applied to the electrodes is usually in the form of a plurality of pulses of relatively short duration.

When these devices are activated, the stimulator produces a series of electrical pulses transferred by the electrodes to the vaginal wall adjacent to the desired muscles causing contraction of these muscles of the pelvic floor. As a result thereof, the external sphincter of the urethra is constricted, preventing the undesired outward flow of urine.

SUMMARY AND OBJECTS OF THE INVENTION

The present invention provides an intravaginal vehicle and associated external recording and stimulation means to provide precise determination of pressures and EMG (electromyography) data. The vehicle is provided with either hydraulic or electrical pressure sensors for detecting the contraction of the pelvic floor muscles. Additionally, a plurality of electrodes are arranged adjacent to the pressure sensors to stimulate the pelvic floor muscles during pressure measurement readings. Calibration marks on the proximal end of the vehicle assist the physician in the determination of the depth of vehicle insertion which provides the greatest contractile force of the muscles as measured from the vaginal orifice.

The invention also consists of a novel method involving a series of steps to be employed for the purpose of determining whether electrical stimulation is feasible and if so, to properly size and fit an intravaginal stimulating device.

A principal object of my invention is to provide an improved and novel intravaginal vehicle for measuring pressures and voltages within the vaginal wall for the purpose of properly fitting an intravaginal stimulator.

A second object of my invention is the provision of a novel and improved method of determining whether intravaginal electrical stimulation will be successful in the treatment of the patient and to determine the proper size and electrode spacing for an appropriate stimulator.

Yet another object of this invention is to provide a trial apparatus for electrical stimulation of the vagina or anus which measures the pressure applied by the muscle being stimulated at the same time that electrical pulse stimulation occurs.

A further object is the provision of a test intravaginal vehicle for electrical stimulator sizing and placement which is of relatively simple construction, and which is safe and convenient to use and which is relatively simple in its application.

Additional, objects, features and advantages of the present invention will become apparent to those skilled in the art from the description which follows of a preferred embodiment taken in conjunction with the accompanying drawings, wherein like reference characters designate like parts in the several views.

DESCRIPTION OF THE PREFERRED EMBODIMENT

Figure 1:
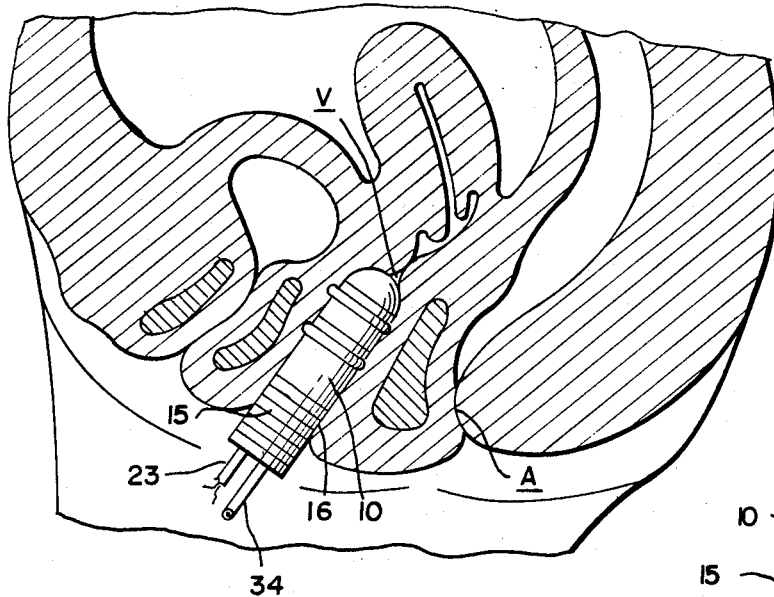
FIG. 1 is a sectional view of the pelvic area of the human female body showing the improved intravaginal vehicle of my invention in place.
Figure 2:
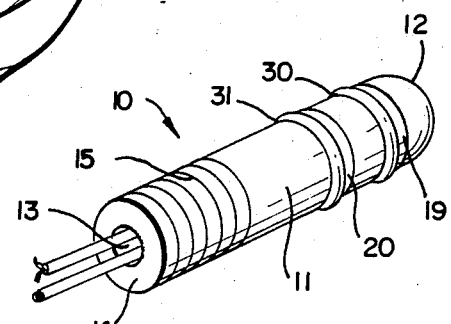
FIG. 2 is an upper rear perspective view of the intravaginal test vehicle.
Figure 3:
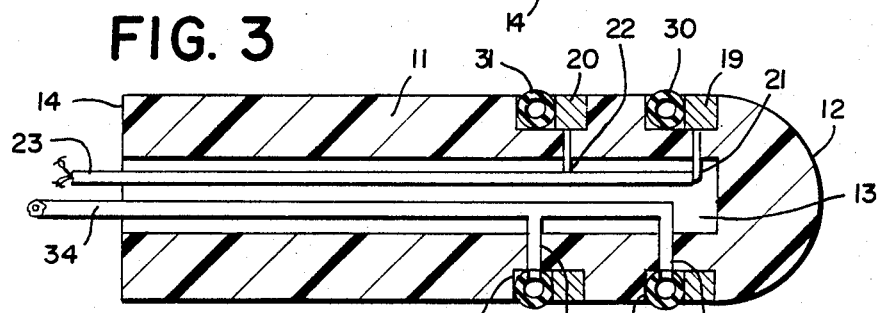
FIG. 3 is an enlarged longitudinal cross-section of the vehicle of FIG. 2.

The present invention consists of an intravaginal vehicle shown broadly at 10 which is adapted for insertion within the vagina V, or in some applications, within the anus A. The vehicle, as best seen in FIGS. 2 and 3, is relatively rigid and includes in the preferred form a silicone rubber cylindrical body 11 having a blunt or rounded head 12 at one end and a longitudinal axial passageway 13 extending from immediately behind the head to the rear face or end 14. For the sake of simplicity, the end 14 of the vehicle will be termed the proximal end and the end having the rounded head 12 will be termed the distal end.

While I have selected silicone rubber as the material of choice for the vehicle 10, any other appropriate insulating material can be used such as a distensible polymer coated with silicone rubber, which may if desired be autoclaved and sterilized.

The body 11 must have sufficient length to accommodate the ranges of vaginal length found in practice. This length should be slightly more than 12 cm to insure utilization in most cases since the average vaginal length is about 9 cm. The proximal end of the vehicle is provided with a series of annular fitting indicia or markers 15 printed or engraved thereon. When the vehicle body is inserted into the vagina, the appropriate marker 15 adjacent the vaginal orifice can be read. The indicia may be in metric or inch scale in order to provide an accurate measurement of insertion depth to determine the position of greatest contractile force of muscle, all as later described.

Figure 4:
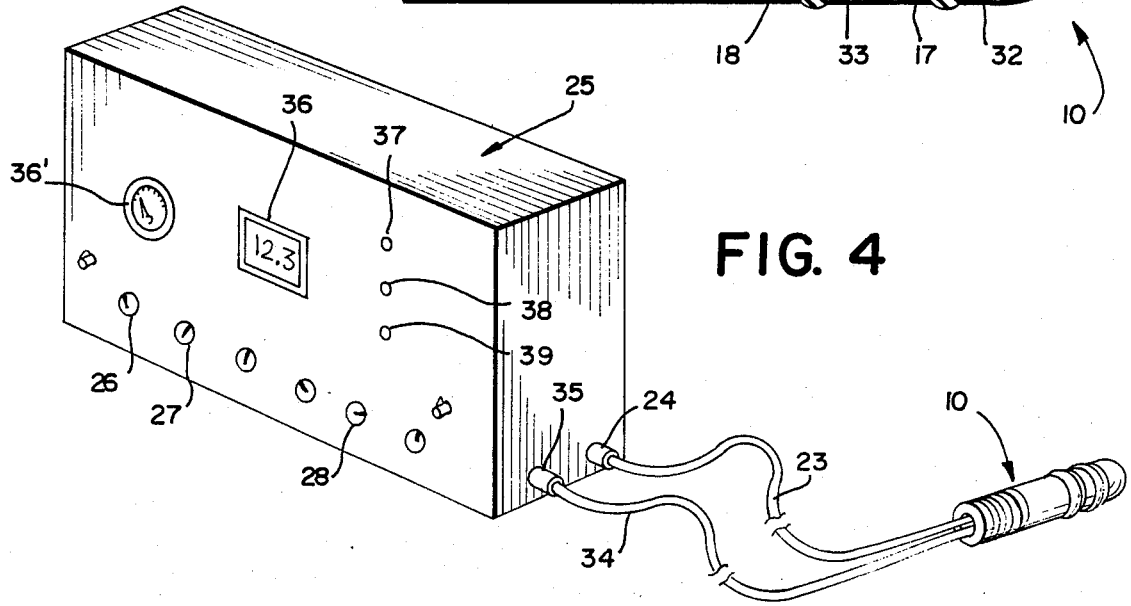
FIG. 4 is a perspective view of the electrical control unit to which the vehicle is attached.

With reference to FIG. 3, it will be seen that two or more circumferential grooves or channels 17 and 18 are formed on the vehicle body 11, spaced proximally of the head 12. A pair of electrodes 19 and 20 are fitted within grooves 17 and 18 and are flush with or slightly elevated above the outer surface of the vehicle body 11. These electrodes are formed of metal or of an electrically conductive polymer and may be about 1 cm in width and have an outside diameter of about 3.2 cm. Each electrode is connected to a lead wire 21, 22 which passes through a radial bore in the body 11 and then passes through the axial passageway 13 as a cable 23 of indefinite length terminating in a plug or jack 24 (see FIG. 4). It will be understood that additional pairs of electrodes may be used if desired for specific situations in practice.

The purpose of the electrodes 19 and 20 is to electrically stimulate the pelvic floor muscles while various pressure recordings and electromyogram (EMG) readings are taken. When more than a single pair of electrodes are used, different pair combinations can be actuated to determine optimum inter-electrode distance and optimal stimulus for a particular patient.

The stimulation parameters of the electrodes are adjustable on the front panel of control unit 25 within certain preset limits. In this regard, amplitude and frequency controls 26 and 27 are provided and switch means 28 may be used to select different pairs of electrodes.

In order to measure pressure adjacent to the vaginal wall, one or more pressure sensors are located at different spaced points along the vehicle longitudinal axis. In the preferred embodiment, annular silicon rings or donuts 30 and 31 are fitted within the grooves 17 and 18 proximal to the electrodes 19 and 20. These rings are filled with a fluid and have an outer diameter slightly larger than the vehicle body diameter so as to insure contact with the vaginal wall. A fluid conducting line 32, 33 extends from each ring through a radial bore in the vehicle body and joins into or is formed integrally with a fluid conduit 34 in the longitudinal passageway 13. Conduit 34 is connected as at coupling 35 to a pressure transducer in the control unit 25 which converts the fluid pressure to an electrical signal in a manner well known in the art.

As will be apparent to those skilled in the art, rings or foils of piezoelectric material with attached electrical connections may also be used for pressure measurement and appropriate amplifiers and filters may be used to process the pressure data to a usable voltage level.

In the preferred embodiment of the invention, the polymer tubing for the sensors are formed into an incomplete ring which is attached to a straight tube and the ring is then adhesively secured in place in the grooves.

In use, the physician measures EMG and pressure data from the digital pressure gauge 36 and the analog EMG gauge 36[1] on the front panel of control unit 25 with the patient voluntarily contracting her pelvic muscles and reproducing symptoms. The recordings are repeated during muscle stimulation by the electrodes 19 and 20. If the pressure is greater at the sensor 30 towards the distal end of the vehicle body 11, then this indicates that it is not placed sufficiently deep in the vaginal orifice. On the other hand, when the pressure is greater at the sensor 31 furthest from the tip toward the proximal end of the vehicle, then this indicates that the body has been inserted too far. When the pressures are substantially equal, then optimum positioning has been achieved insuring proper electrode placement in the final vehicle to be provided to the patient. A series of panel light indicators have been provided in the control unit front panel to assist the physician. By feeding the pressure signals from two points after processing into a comparator with variable sensitivity, the indicator 37 will show if the vehicle is in too far. Indicator light 38 will illuminate if the vehicle is not sufficiently inserted, and indicator 39 will signal a balance of pressures and proper insertion depth. This should be done during either voluntary or stimulated contraction of the pelvic floor muscles. A variable resistor inside of the control unit 25 may be adjusted to determine the limits of equal pressure.

Stimulation of the pelvic floor muscles electrically should be accomplished while the pressure readings are recorded. As indicated above, the stimulus parameters are readily adjustable on the front panel by controls 26 and 27 and may be varied within preset limits. The pressure information is processed from a pressure gauge or electrical transducer, all as known in the art, and the force of contraction then recorded is displayed on the front panel of unit 25. A jack plug, not shown, connected to the back panel can carry this signal through an interface to an analog or digital external recorder or computer.

During use, EMG (electromyogram) is recorded by the physician while pressure readings are taken. The raw EMG signal is processed using analog or digital circuitry and the processed signal is displayed on the front panel. Again, jack plugs on the back panel to interface with an analog or digital recorder or computer.

It has been found in practice that the system of my invention may be used to obtain diagnostic information concerning the patient's neuromuscular, urinary, sexual and other body sub-systems. For example, the compliance of the vagina may be determined by forcing a volume of fluid into the chamber and determining the change in pressure according to the known formula of Compliance=change in volume divided by change in pressure. An automatic syringe may be incorporated to force fluid into the line which is connected to the vehicle. The same system may be used to determine thresholds for electrical stimulation parameters, pressures, and EMG at which symptoms occur in the patient and when progress is made in terms of increasing the force produced by the pelvic muscles as treatment is rendered. It will be apparent to the physician whether or not the patient will be assisted by electrical stimulation, or if unwanted effects will result at the sites tested.

The vehicle of the invention may be used in conjunction with drug therapy, electrical or mechanical stimulation at other sites, both cutaneously with stimulating pads over peripheral nerves or during surgery with direct stimulation of the nerves. For example electrode stimulator pads may be adhesively attached to the skin, such as on the leg, to obtain a reflex reaction of the sphincter, in conjunction with body cavity stimulation via the vehicle.

As an additional diagnostic tool an ultrasound transducer may be included within the vehicle to obtain a picture of the surrounding tissue. The hardware to be used in this embodiment is well known in the prior art of diagnostic medicine.

The foregoing description of the preferred embodiments of the invention is given merely by way of illustration and various modifications, which will be apparent to those skilled in this art, may be adopted without departure from the scope of my invention. This is especially true with regard to choice of materials and specific electrical circuitry within the control unit 25, whose functions may be accomplished in a large variety of ways.

What is claimed is:

1. Apparatus for electrically stimulating the muscles surrounding a body cavity and for measuring body cavity pressure during such stimulation for properly fitting a patient with an electrical stimulator treatment device, comprising an elongated cylindrical vehicle, said vehicle being substantially rigid and adapted to fit within the body cavity, a plurality of circumferential electrodes spaced along the vehicle and adapted to contact the body cavity wall, means for selectively providing an electrical voltage to selected ones of said electrodes to stimulate the muscles adjacent the body cavity, pressure transducer means mounted on said vehicle adjacent said electrodes for sensing cavity wall pressure wherein the optimum position of said vehicle in said cavity is determined by sensing the response to stimulation, and means for reading said pressure.

2. An apparatus as defined in claim 1, wherein the electrical voltage provided is in the form of a plurality of pulses of relatively short duration, and further including means to adjust the amplitude and the frequency of said pulses.

3. An apparatus as defined in claim 1, and further including scale markings on the vehicle adjacent the proximal end to measure vehicle insertion depth within the body cavity at the point of optimum positioning of said vehicle through said pressure reading.

4. Apparatus for use in fitting a patient with an electrical body cavity stimulator comprising, an elongated cylindrical vehicle adapted for insertion in a body cavity, said vehicle being substantially rigid and carrying a plurality of axially spaced circumferential electrodes along a portion of its length, said electrodes adapted to contact the wall of the patient's body cavity, pressure transducer mounted on said vehicle adjacent said electrodes for sensing cavity wall pressure wherein the optimum position of said vehicle in said cavity is determined by sensing the response to stimulation, a control unit external of said vehicle, said control unit including means for selectively providing an electrical voltage to selected ones of said electrodes, conductor means for connecting said electrodes to means for providing electrical voltage, and gauge means on said control unit to provide a reading of pressure from a selected transducer.

5. Apparatus as defined in claim 4, wherein the means for providing an electrical voltage, supplies said voltage in the form of a plurality of pulses of relatively short duration, and means are further provided in the control unit to selectively adjust the amplitude and the frequency of said pulses.

6. Apparatus as defined in claim 4, and further including scale markings on the vehicle adjacent the proximal end to measure vehicle insertion depth within the body cavity at the point of optimum positioning of said vehicle through said pressure reading.

7. A method for fitting a patient with a body cavity electrical stimulator, comprising the steps of, inserting an elongate vehicle within the cavity to a selected depth, said vehicle provided with spaced means along its length for providing a pulsing electrical stimulation to the adjacent body cavity wall and with spaced pressure measuring means also along its length, applying electrical stimulation to the patient through a selected pair of said spaced means, measuring the pressure generated by a selected pair of pressure measuring means, changing the depth of vehicle insertion until the measured pressures are substantially equal, and measuring the depth of vehicle insertion that provided the equal pressures.

8. A method as defined in claim 7, and further including the step of measuring the electromyography (EMG) during the period of electrical stimulation.

9. A method as defined in claim 7, wherein the elongate vehicle is inserted in the vagina.

10. A method as defined in claim 7, wherein the elongate vehicle is inserted in the anus.

11. Apparatus for electrically stimulating the muscles surrounding a body cavity and for measuring body cavity pressure during such stimulation for properly fitting a patient with an electrical stimulator treatment device, comprising an elongated cylindrical vehicle, said vehicle being substantially rigid and adapted to fit within the body cavity, a plurality of circumferential electrodes spaced along the vehicle and adapted to contact the body cavity wall, means for selectively providing an electrical voltage to selected ones of said electrodes to stimulate the muscles adjacent the body cavity, pressure transducer means mounted on said vehicle adjacent said electrodes for sensing cavity wall pressure, means for reading said pressure, said means for providing an electrical voltage being external to said vehicle and further including an axial passageway extending longitudinally within the vehicle, electrical conductor means connected to each electrode, said conductor means passing through said passageway and extending out of said vehicle and being connected to said means for providing an electrical voltage, said pressure transducer means comprising a plurality of substantially annular hollow rings of expandable material, said rings each filled with a fluid, and conduit means connecting said rings to said means for reading pressure.

12. Apparatus for use in fitting a patient with an electrical body cavity stimulator comprising, an elongated cylindrical vehicle adapted for insertion in a body cavity, said vehicle being substantially rigid and carrying a plurality of axially spaced circumferential electrodes along a portion of its length, said electrodes adapted to contact the wall of the patient's body cavity, pressure transducer mounted in said vehicle adjacent said electrodes for sensing cavity wall pressure and a control unit external of said vehicle, said control unit including means for selectively providing an electrical voltage to selected ones of said electrodes, conductor means for connecting said electrodes to means for providing electrical voltage, and gauge means on said control unit to provide a reading of pressure from a selected transducer, said vehicle further including an axial passageway extending longitudinally within said vehicle, said conductor means passing through said passageway, and conduit means extending through said passageway for connecting said pressure transducers to said gauge means.

13. Apparatus for use in fitting a patient with an electrical body cavity stimulator comprising, an elongated cylindrical vehicle adapted for insertion in a body cavity, said vehicle being substantially rigid and carrying a plurality of axially spaced circumferential electrodes along a portion of its length, said electrodes adapted to contact the wall of the patient's body cavity, pressure transducer mounted in said vehicle adjacent said electrodes for sensing cavity wall pressure and a control unit external of said vehicle, said control unit including means for selectively providing an electrical voltage to selected ones of said electrodes, conductor means for connecting said electrodes to means for providing electrical voltage, gauge means on said control unit to provide a reading of pressure from a selected transducer, and said vehicle body being formed with a plurality of circumferential channels, said electrodes and said pressure transducer means each fitting within separate channels.

14. Apparatus for use in fitting a patient with an electrical body cavity stimulator comprising, an elongated cylindrical vehicle adapted for insertion in a body cavity, said vehicle being substantially rigid and carrying a plurality of axially spaced circumferential electrodes along a portion of its length, said electrodes adapted to contact the wall of the patient's body cavity, pressure transducer means mounted on said vehicle adjacent said electrodes for sensing cavity wall pressure, a control unit external of said vehicle, said control unit including means for selectively providing an electrical voltage to selected ones of said electrodes, conductor means for connecting said electrodes to means for providing electrical voltage, gauge means on said control unit to provide a reading of pressure from a selected transducer, said vehicle further including an axial passageway extending longitudinally within the vehicle, said conductor means passing through said passageway, conduit means extending through said passageway for connecting said pressure transducers to said gauge means, and said pressure transducer means comprising a plurality of substantially annular hollow rings of expandable material, said rings each filled with a fluid.

15. Apparatus for use in fitting a patient with an electrical body cavity stimulator comprising, an elongated cylindrical vehicle adapted for insertion in a body cavity, said vehicle being substantially rigid and carrying a plurality of axially spaced circumferential electrodes along a portion of its length, said electrodes adapted to contact the wall of the patient's body cavity, pressure transducer mounted in said vehicle adjacent said electrodes for sensing cavity wall pressure, a control unit external of said vehicle, said control unit including means for selectively providing an electrical voltage to selected ones of said electrodes, conductor means for connecting said electrodes to means for providing electrical voltage, gauge means on said control unit to provide a reading of pressure from a selected transducer, said vehicle further including an axial passageway extending longitudinally within the vehicle, said conductor means passing through said passageway, conduit means extending through said passageway for connecting said pressure transducers to said gauge means, said pressure transducer means comprising a plurality of substantially annular hollow rings of expandable material, said rings each filled with a fluid, and further including means on said control unit for providing a reading of electromography (EMG).

* * * * *